(12) United States Patent
Stopek et al.

(10) Patent No.: US 8,858,592 B2
(45) Date of Patent: Oct. 14, 2014

(54) WOUND PLUGS

(75) Inventors: Joshua Stopek, Guilford, CT (US);
Gregory Fischvogt, Hamden, CT (US);
Timothy Sargeant, Guilford, CT (US)

(73) Assignee: Covidien LP, Mansfield, MA (US)

( * ) Notice: Subject to any disclaimer, the term of this patent is extended or adjusted under 35 U.S.C. 154(b) by 530 days.

(21) Appl. No.: 12/914,382

(22) Filed: Oct. 28, 2010

(65) Prior Publication Data

US 2011/0125185 A1 May 26, 2011

Related U.S. Application Data

(60) Provisional application No. 61/263,959, filed on Nov. 24, 2009.

(51) Int. Cl.
*A61B 17/08* (2006.01)
*A61B 17/00* (2006.01)

(52) U.S. Cl.
CPC ... *A61B 17/0057* (2013.01); *A61B 2017/00637* (2013.01); *A61B 2017/00004* (2013.01)
USPC ........................................................ 606/213

(58) Field of Classification Search
CPC ................. A61B 17/0057; A61B 2017/00637; A61B 2017/00004
USPC ..................... 606/95, 213, 232, 151; 128/831
See application file for complete search history.

(56) References Cited

U.S. PATENT DOCUMENTS

| | | |
|---|---|---|
| 5,116,357 A | 5/1992 | Eberbach |
| 5,147,374 A | 9/1992 | Fernandez |
| 5,162,430 A | 11/1992 | Rhee et al. |
| 5,192,301 A | 3/1993 | Kamiya et al. |
| 5,254,105 A | 10/1993 | Haaga |
| 5,258,000 A | 11/1993 | Gianturco |
| 5,324,775 A | 6/1994 | Rhee et al. |
| 5,326,350 A | 7/1994 | Li |
| 5,334,216 A * | 8/1994 | Vidal et al. ............... 606/213 |
| 5,370,660 A | 12/1994 | Weinstein et al. |
| 5,410,016 A | 4/1995 | Hubbell et al. |
| 5,439,469 A | 8/1995 | Heaven et al. |
| 5,458,570 A * | 10/1995 | May, Jr. .................. 604/500 |
| 5,478,352 A | 12/1995 | Fowler |
| 5,514,379 A | 5/1996 | Weissleder et al. |

(Continued)

FOREIGN PATENT DOCUMENTS

| | | |
|---|---|---|
| EP | 2 143 737 A1 | 1/2010 |
| EP | 2 196 193 A1 | 6/2010 |

(Continued)

OTHER PUBLICATIONS

European Search Report for EP 12169360.0-1269 dated Jun. 15, 2012 (6 pages).

(Continued)

*Primary Examiner* — Corrine M McDermott
*Assistant Examiner* — Son Dang

(57) ABSTRACT

A medical device for wound closure, including an elongate body with a plurality of portions and a perforated region disposed therebetween. The medical device may also include an alignment member. The wound plug may also have a first position for insertion, the portions being mechanically coupled to each other, and a second position where one or more of the portions are spatially separated.

14 Claims, 4 Drawing Sheets

(56) References Cited

U.S. PATENT DOCUMENTS

| | | | |
|---|---|---|---|
| 5,522,846 A * | 6/1996 | Bonutti | 606/232 |
| 5,531,759 A | 7/1996 | Kensey et al. | |
| 5,534,012 A * | 7/1996 | Bonutti | 606/232 |
| 5,543,441 A | 8/1996 | Rhee et al. | |
| 5,545,178 A * | 8/1996 | Kensey et al. | 606/213 |
| 5,550,187 A | 8/1996 | Rhee et al. | |
| 5,584,862 A * | 12/1996 | Bonutti | 606/232 |
| 5,601,602 A | 2/1997 | Fowler | |
| 5,630,833 A | 5/1997 | Katsaros et al. | |
| 5,733,306 A * | 3/1998 | Bonutti | 606/232 |
| 5,752,974 A | 5/1998 | Rhee et al. | |
| 5,845,645 A * | 12/1998 | Bonutti | 128/898 |
| 5,874,500 A | 2/1999 | Rhee et al. | |
| 5,904,703 A | 5/1999 | Gilson | |
| 5,941,900 A * | 8/1999 | Bonutti | 606/232 |
| 6,077,292 A * | 6/2000 | Bonutti | 606/232 |
| 6,090,996 A | 7/2000 | Li | |
| 6,126,675 A | 10/2000 | Shchervinsky et al. | |
| 6,152,943 A | 11/2000 | Sawhney | |
| 6,165,201 A | 12/2000 | Sawhney et al. | |
| 6,179,862 B1 | 1/2001 | Sawhney | |
| 6,391,060 B1 | 5/2002 | Ory et al. | |
| 6,482,179 B1 | 11/2002 | Chu et al. | |
| 6,514,534 B1 | 2/2003 | Sawhney | |
| 6,566,406 B1 | 5/2003 | Pathak et al. | |
| 6,605,294 B2 | 8/2003 | Sawhney | |
| 6,656,200 B2 | 12/2003 | Li et al. | |
| 6,663,655 B2 * | 12/2003 | Ginn et al. | 606/213 |
| 6,673,093 B1 | 1/2004 | Sawhney | |
| 6,703,047 B2 | 3/2004 | Sawhney et al. | |
| 6,755,868 B2 | 6/2004 | Rousseau | |
| 6,818,018 B1 | 11/2004 | Sawhney | |
| 6,846,319 B2 | 1/2005 | Ginn et al. | |
| 6,916,483 B2 | 7/2005 | Ralph | |
| 6,964,674 B1 | 11/2005 | Matsuura et al. | |
| 7,009,034 B2 | 3/2006 | Pathak et al. | |
| 7,328,707 B2 | 2/2008 | Durgin | |
| 7,331,981 B2 | 2/2008 | Cates et al. | |
| 7,335,220 B2 | 2/2008 | Khosravi et al. | |
| 7,338,517 B2 | 3/2008 | Yost et al. | |
| 7,347,850 B2 | 3/2008 | Sawhney | |
| 7,416,546 B2 | 8/2008 | Pugsley et al. | |
| 7,682,400 B2 * | 3/2010 | Zwirkoski | 623/23.48 |
| 7,691,115 B2 | 4/2010 | Corcoran et al. | |
| 7,850,710 B2 | 12/2010 | Huss | |
| 2002/0165581 A1 | 11/2002 | Brucker | |
| 2004/0215231 A1 | 10/2004 | Fortune | |
| 2005/0155608 A1 | 7/2005 | Pavcnik et al. | |
| 2005/0267528 A1 | 12/2005 | Ginn | |
| 2006/0015142 A1 | 1/2006 | Malazgirt | |
| 2006/0142797 A1 | 6/2006 | Egnelov | |
| 2007/0083268 A1 | 4/2007 | Teoh | |
| 2007/0150002 A1 | 6/2007 | Szabo et al. | |
| 2007/0198059 A1 | 8/2007 | Patel et al. | |
| 2007/0219583 A1 | 9/2007 | Sing et al. | |
| 2008/0004657 A1 | 1/2008 | Obermiller et al. | |
| 2008/0051831 A1 * | 2/2008 | Deal et al. | 606/213 |
| 2008/0114092 A1 | 5/2008 | Sawhney | |
| 2008/0215087 A1 | 9/2008 | Pavcnik et al. | |
| 2008/0312683 A1 | 12/2008 | Drasler et al. | |
| 2009/0012558 A1 | 1/2009 | Chen et al. | |
| 2009/0069843 A1 | 3/2009 | Agnew | |
| 2010/0076463 A1 * | 3/2010 | Mavani et al. | 606/151 |

FOREIGN PATENT DOCUMENTS

| | | |
|---|---|---|
| EP | 2 233 160 A2 | 9/2010 |
| EP | 2 233 161 A2 | 9/2010 |
| WO | 2006009925 A2 | 1/2006 |
| WO | WO 2008/055197 A2 | 5/2008 |

OTHER PUBLICATIONS

European Search Report for EP 06016963.8-2318 date of completion is Mar. 9, 2007 (9 pages).
International Search Report issued in Application EP 11250562.3 mailed Dec. 8, 2011.
International Search Report issued in Application EP 11250564.9 mailed Dec. 8, 2011.
International Search Report issued in Application EP 11250563.1 mailed Dec. 27, 2011.
International Search Report issued in Application EP 11250566.4 mailed Dec. 22, 2011.
International Search Report issued in Application EP 11250565.6 mailed Dec. 23, 2011.

* cited by examiner

WOUND PLUGS

CROSS-REFERENCE TO RELATED APPLICATIONS

This application claims the benefit of and priority to U.S. Provisional Patent Application No. 61/263,959, filed Nov. 24, 2009, the entire disclosure of which is incorporated herein by reference.

TECHNICAL FIELD

The present disclosure relates to an implant for providing closure to wounds and, more specifically, to a wound plug for repairing and sealing perforations in tissue, such as trocar wounds from laparoscopic port sites.

BACKGROUND OF RELATED ART

A variety of surgical procedures, for example, laparoscopic procedures, are performed through an access port, during which the access device punctures the tissue to provide access to the surgical site.

A hernia is a protrusion of a tissue, structure, or part of an organ through injured muscle tissue or an injured membrane by which the tissue, structure, or organ is normally contained. Trocar site herniation is a potential complication of minimally invasive surgery. Upon removal of a minimally invasive surgical device or the access port, tissues may not properly heal and can present concerns including reherniation. More specifically, omental and intestinal herniation has been reported with larger trocar sites (10 mm).

Currently, wound closure devices, such as sutures, are used to close various layers of tissue post-surgery. Suturing a patient after removal of an access device may be cumbersome, while accumulating additional costs to the patient such as increased time spent in the operating room.

While conventional methods such as suturing exist, improvements in the field are desired.

SUMMARY

The present disclosure is directed to a wound plug including an elongate body comprising portions and a perforated region disposed therebetween. In certain embodiments, the elongate body has a first position for insertion wherein the portions are connected to each other via the perforated region; and, the elongate body has a second position wherein the portions are spatially separated. In the second position, the portions are vertically and/or horizontally spatially separated. The portions may be spatially separated due to forced exerted thereon by the movement of at least one tissue plane.

More specifically, the perforated region includes perforations which may extend generally parallel to a tissue plane. The perforations may also extend along a horizontal axis of the elongate body. In other embodiments, the perforations extend across the thickness of the elongate body.

In some embodiments, the wound plug includes at least three portions. The portions include a distal portion and a proximal portion. The distal portion may further comprise a mesh.

The elongate body includes a shape which may include cylindrical, oval, spherical, rectangular, trapezoidal, or polygonal.

Further, the wound plug may comprise nucleophilic and electrophilic polymers.

In another embodiment, the wound plug includes an elongate body comprising portions, wherein the elongate body has a first position wherein the portions are mechanically coupled to each other, and the elongate body has a second position wherein the portions are spatially separated. The wound plug may further comprise an alignment member which may be a sheath, sleeve, adhesive, solvent, glue, fiber, or suture.

The portions may comprise a monomer or polymer disposed therebetween. In other embodiments, the portions are mechanically coupled by a removable sleeve. In yet alternate embodiments, the portions are mechanically coupled by a water soluble polymer.

At least one of the portions may further comprise a mesh.

BRIEF DESCRIPTION OF DRAWINGS

The illustrative embodiments described herein will become more readily apparent from the following description, reference being made to the accompanying drawings in which.

DETAILED DESCRIPTION OF EMBODIMENTS

Figure 1A:
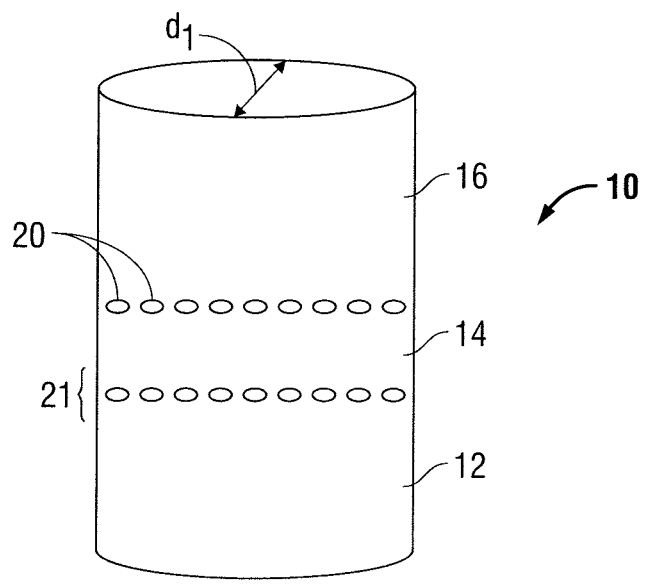
FIG. 1A illustrates one embodiment of a wound plug in accordance with the present disclosure.

The present disclosure is directed to wound plugs for use in tissue repair, and more particularly for repair of trocar site wounds. The wound plug may include an elongate body having multiple separable portions with a perforated region disposed therebetween. In some embodiments, once implanted, tissue planes may shift, spatially separating the portions of the wound plug. The portions may provide support, which may be unique to the different tissue planes/layers. In other embodiments, the portions are mechanically coupled to one another. In further embodiments, the portions may further include an alignment member such as an adhesive, sealant, sheath, fiber, suture, and/or sleeve. Upon movement of tissue planes in vivo, portions of the wound plug spatially separate.

Wound plugs, may be fabricated from biodegradable, non-biodegradable, natural and synthetic materials, and combinations thereof. The term "biodegradable" as used herein includes both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

Suitable materials used to construct wound plugs of the present disclosure, include both non-biodegradable and biodegradable polymers. Suitable non-biodegradable materials which may be useful in the present disclosure include but are not limited to fluorinated polymers such as fluoroethylenes and fluoroPEGs; polyolefins such as polyethylene (including ultra high molecular weight polyethylene (UHMWPE)) and polypropylene; polyesters such as poly ethylene terepththalate (PET); nylons; polyamides; polyurethanes; silicones; polybutesters; polyethylene glycols and polyethylene oxides; polyaryletherketone; copolymers and combinations thereof. Additionally, non-biodegradable polymers and monomers may be combined with each other and may also be combined with various biodegradable polymers and monomers to create the wound plugs.

Suitable synthetic biodegradable materials include but are not limited to polymers including aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); (3-hydroxypropionate; polyimide carbonates, poly(imino carbonates) such as such as poly (bisphenol A-iminocarbonate) and the like; polyorthoesters; polyoxaesters including those containing amine groups; polyphosphazenes; poly (propylene fumarates); polyurethanes; dimethylsulfoniopropionate (DMSP); polymer drugs such as polydiflunisol, polyaspirin, and protein therapeutics; biologically modified (e.g., protein, peptide) bioabsorbable polymers; and copolymers, block copolymers, homopolymers, blends, and combinations thereof. Polymer drugs referenced hereinabove may include polymers wherein the backbone comprises a polymer drug, or in the alternative, polymer drugs may comprise polymers in which the pendant groups or side chains comprise polymer drugs. Degradable polymer drugs may also comprise polymers including but not limited to polyanhydrides, polyesters, poly (ether esters), polyamines, polyamide esters, and combinations thereof.

More specifically, for the purpose of this invention, aliphatic polyesters include, but are not limited to, homopolymers and copolymers of lactide (which includes lactic acid, D-,L- and meso lactide); glycolide (including glycolic acid); epsilon-caprolactone; p-dioxanone (1,4-dioxan-2-one); trimethylene carbonate (1,3-dioxan-2-one); alkyl derivatives of trimethylene carbonate; Δ-valerolactone; p-butyrolactone; γ-butyrolactone; s-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; a, a diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof.

Natural polymers may also be used in accordance with the present disclosure, non-limiting examples include, proteins such as collagen, gelatin, albumin, serum, and casein; poly (amino acids); polysaccharides such as cellulose (including carboxymethyl cellulose), dextran, chitin, chitosan, alginate and hyaluronic acid; glycosaminoglycans; gut; chemical derivatives thereof (substitutions and/or additions of chemical groups, for example, alkyl, alkylene, hydroxylations, oxidations, and other modifications routinely made by those skilled in the art); and copolymers and combinations thereof. Collagen as used herein includes natural collagen such as animal derived collagen, or synthetic collagen such as recombinant collagen. Additionally, natural materials include chemical modifications of the above-listed materials such as recombinant, aminated, sulfonated, and carboxylated polymer analogs. Natural polymers may be combined with synthetic polymers, both biodegradable and non-biodegradable to create wound plugs of the present disclosure.

More specifically, synthetically modified natural polymers include polysaccharide and cellulose derivatives such as alkyl celluloses, hydroxyalkyl celluloses, cellulose ethers, cellulose esters, and nitrocelluloses. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These may be collectively referred to herein, in embodiments, as "celluloses."

In some embodiments, hydrophilic polymers may be used. Suitable hydrophilic polymers include but are not limited to anionic, cationic and neutral monomers and polymers of vinyl polymers such as polyvinyl alcohol, polyvinyl methyl ether, polyvinylpyrrolidone (PVP), poly acrylic acid, styrene sulfonic acid, polyhydroxyethylmethylacrylate (pHEMA) and phospholipid vinyls; acrylic polymers such as sodium polyacrylate, polyethylacrylate, and polyacrylamide; polyethylene glycol, polypropylene oxide, and polypropylene glycol and homopolymers and copolymers thereof; phosphorylcholine functional acrylates and methacrylates; and homopolymers and copolymers thereof.

In some embodiments, the wound plugs may be formed from a hydrogel. Hydrogels of the present disclosure may uptake fluids and swell from about 5% to about 100%, in embodiments, from about 20% to about 80% by volume. The swellable nature of a hydrogel may enable a more secure and conformed fit into the tissue defect. Suitable materials include, but are not limited to, degradable or modified polymers/copolymers including those hydrophilic polymers mentioned herein, and/or any other biocompatible vinyl monomers or polymers and combinations thereof. The above materials may be prepared by methods known to those skilled in the art including the use of a degradable crosslinker.

In one embodiment, a pre-formed hydrogel may be used to create a wound plug. The hydrogel may be formed of any components within the purview of those skilled in the art. In some embodiments, as discussed further below, the hydrogel may be formed of natural components such as collagen, gelatin, serum, hyaluronic acid, combinations thereof, and the like. In some embodiments, the natural component may be released at the site of implantation as any hydrogel utilized as part of the wound closure device degrades. The term "natural component" as used herein includes polymers, compositions of matter, materials, combinations thereof, and the like, which can be found in nature or derived from compositions/organisms found in nature. Natural components also may include compositions which are found in nature but can be synthesized by man, for example, using methods to create natural/synthetic/biologic recombinant materials, as well as methods capable of producing proteins with the same sequences as those found in nature, and/or methods capable of producing materials with the same structure and components as natural materials, such as synthetic hyaluronic acid, which is commercially available, for example, from Sigma Aldrich.

The hydrogels may be formed from a single precursor or multiple precursors. This may occur prior to implantation or at the time of implantation. In either case, the formation of the hydrogel may be accomplished by having a precursor that can be activated at the time of application to create, in embodiments, a hydrogel. Activation can be through a variety of methods including, but not limited to, environmental changes such as pH, ionicity, pressure, and temperature. In other embodiments, the components for forming a hydrogel may be contacted outside the body, such as a pre-formed wound closure device or component thereof. Where the hydrogel is formed from multiple precursors, for example two precursors, the precursors may be referred to as a first and second hydrogel precursor. The terms "first hydrogel precursor" and "second hydrogel precursor" each mean a polymer, functional polymer, macromolecule, small molecule, or crosslinker that can take part in a reaction to form a network of crosslinked molecules, e.g., a hydrogel.

In embodiments, the precursor utilized to form the hydrogel may be a monomer or a macromer. One type of precursor may have a functional group that is an electrophile or nucleophile. Electrophiles react with nucleophiles to form covalent bonds. Covalent crosslinks or bonds refer to chemical groups formed by reaction of functional groups on different polymers that serve to covalently bind the different polymers to each other. In certain embodiments, a first set of electrophilic functional groups on a first precursor may react with a second set of nucleophilic functional groups on a second precursor. When the precursors are mixed in an environment that permits a reaction (e.g., as relating to pH, temperature, ionicity, and/or solvent), the functional groups react with each other to form covalent bonds. The precursors become crosslinked when at least some of the precursors can react with more than one other precursor. For instance, a precursor with two functional groups of a first type may be reacted with a crosslinking precursor that has at least three functional groups of a second type capable of reacting with the first type of functional groups.

The term "functional group" as used herein refers to groups capable of reacting with each other to form a bond. In embodiments, such groups may be electrophilic or nucleophilic. Electrophilic functional groups include, for example, N-hydroxysuccinimides, sulfosuccinimides, carbonyldiimidazole, sulfonyl chloride, aryl halides, sulfosuccinimidyl esters, N-hydroxysuccinimidyl esters, succinimidyl esters, epoxides, aldehydes, maleimides, imidoesters and the like. In certain embodiments, the electrophilic functional group is a succinimidyl ester. The first and second hydrogel precursors may have biologically inert and water soluble cores. More specifically, the electrophilic hydrogel precursors may have biologically inert and water soluble cores, as well as non-water soluble cores. When the core is a polymeric region that is water soluble, suitable polymers that may be used include: polyethers, for example, polyalkylene oxides such as polyethylene glycol("PEG"), polyethylene oxide ("PEO"), polyethylene oxide-co-polypropylene oxide ("PPO"), co-polyethylene oxide block or random copolymers, and polyvinyl alcohol ("PVA"); polyvinyl pyrrolidinone) ("PVP"); poly (amino acids); poly(saccharides), such as dextran, chitosan, alginates, carboxymethylcellulose, oxidized cellulose, hydroxyethylcellulose, hydroxymethylcellulose; hyaluronic acid; and proteins such as albumin, collagen, casein, and gelatin. Other suitable hydrogels may include components such as methacrylic acid, acrylamides, methyl methacrylate, hydroxyethyl methacrylate, combinations thereof, and the like.

The polyethers, and more particularly poly(oxyalkylenes) or polyethylene glycol, may be utilized in some embodiments. When the core is small in molecular nature, any of a variety of hydrophilic functionalities can be used to make the first and second hydrogel precursors water soluble. For example, functional groups like hydroxyl, amine, sulfonate and carboxylate, which are water soluble, may be used to make the precursor water soluble. For example, the n-hydroxysuccinimide ("NHS") ester of subaric acid is insoluble in water, but by adding a sulfonate group to the succinimide ring, the NHS ester of subaric acid may be made water soluble, without affecting its reactivity towards amine groups. In embodiments, the precursor having electrophilic functional groups may be a PEG ester.

As noted above, each of the first and second hydrogel precursors may be multifunctional, meaning that they may include two or more electrophilic or nucleophilic functional groups, such that, for example, a nucleophilic functional group on the first hydrogel precursor may react with an electrophilic functional group on the second hydrogel precursor to form a covalent bond. At least one of the first or second hydrogel precursors includes more than two functional groups, so that, as a result of electrophilic-nucleophilic reactions, the precursors combine to form cross-linked polymeric products.

A macromolecule having the electrophilic functional group may be multi-armed. For example, the macromolecule may be a multi-armed PEG having four, six, eight, or more arms extending from a core. The core may be the same or different from the macromolecule forming the arms. For example, the core may be PEG and the multiple arms may also be PEG. In embodiments, the core may be a natural polymer.

The molecular weight (MW) of the electrophilic crosslinker may be from about 2,000 g/mol to about 100,000 g/mol; in embodiments from about 10,000 g/mol to about 40,000 g/mol. Multi-arm precursors may have a molecular weight that varies depending on the number of arms. For example, an arm having a 1000 g/mol of PEG has enough $CH_2CH_2O$ groups to total at least 1000 g/mol. The combined molecular weight of an individual arm may be from about 250 g/mol to about 5,000 g/mol; in embodiments from about 1,000 g/mol to about 3,000 g/mol; in embodiments from about 1,250 g/mol to about 2,500 g/mol. In embodiments, the electrophilic crosslinker may be a multi-arm PEG functionalized with multiple NHS groups having, for example, four, six or eight arms and a molecular weight from about 5,000 g/mol to about 25,000 g/mol. Other examples of suitable precursors are described in U.S. Pat. Nos. 6,152,943; 6,165, 201; 6,179,862; 6,514,534; 6,566,406; 6,605,294; 6,673,093; 6,703,047; 6,818,018; 7,009,034; and 7,347,850, the entire disclosures of each of which are incorporated herein by reference.

The electrophilic precursor may be a cross-linker that provides an electrophilic functional group capable of bonding with nucleophiles on another component, such as, in certain embodiments, a natural component containing primary amines. The natural component may be endogenous to the patient (e.g., collagen), to which the electrophilic crosslinker is applied.

In embodiments, one of the precursors may be a nucleophilic precursor possessing nucleophilic groups. Nucleophilic groups which may be present include, for example, $-NH_2$, $-SH$, $-OH$, $-PH_2$, and $-CO-NH-NH_2$. Any monomer, macromer, polymer, or core described herein as suitable for use in forming the electrophilic precursor may be functionalized with nucelophilic groups to form a nucleophilic precursor. In other embodiments, a natural component possessing nucleophilic groups such as those listed above may be utilized as the nucleophilic precursor.

The natural component may be, for example, collagen, gelatin, blood (including serum, which may be whole serum or extracts therefrom), hyaluronic acid, proteins, albumin, other serum proteins, serum concentrates, platelet rich plasma (prp), combinations thereof, and the like. Additional suitable natural components which may be utilized or added to another natural component include, for example, stem cells, DNA, RNA, enzymes, growth factors, peptides, polypeptides, antibodies, other nitrogenous natural molecules, combinations thereof, and the like. Other natural components may include derivatives of the foregoing, for example modified polysaccharides such as hyaluronic acid or dextran, which may be naturally derived, synthetic, or biologically derived. For example, in some embodiments, the natural component may be aminated hyaluronic acid.

As previously mentioned, any of the above natural components may be synthetically prepared, e.g., synthetic hyaluronic acid, which may be purchased from Sigma Aldrich, for example. Similarly, in embodiments the natural component could be a natural or synthetic long chain aminated polymer.

The natural component may provide cellular building blocks or cellular nutrients to the tissue that it contacts in situ. For example, serum contains proteins, glucose, clotting factors, mineral ions, and hormones which may be useful in the formation or regeneration of tissue.

In certain embodiments, the natural component includes whole serum. In some embodiments, the natural component is autologous, such as collagen, serum, blood, and the like.

A multifunctional nucleophilic polymer, such as a natural component having multiple amine groups, may be used as a first hydrogel precursor and a multifunctional electrophilic polymer, such as a multi-arm PEG functionalized with multiple NHS groups, e.g., a PEG ester, may be used as a second hydrogel precursor. The precursors may be in solution(s), which may be combined to permit formation of the hydrogel. Any solutions utilized as part of the in situ forming material system should not contain harmful or toxic solvents. The precursor(s) may be substantially soluble in a solvent such as water to allow application in a physiologically-compatible solution, such as buffered isotonic saline.

More specifically, a pre-formed hydrogel may be formed from a combination of collagen and gelatin as the natural component, with a multi-functional PEG utilized as a crosslinker. The collagen and gelatin may be placed in solution, utilizing a suitable solvent. To this solution, hyaluronic acid may be added along with a high pH buffer. Such a buffer may have a pH from about 8 to about 12, in embodiments from about 8.2 to about 9. One suitable non-limiting buffer is a borate buffer.

In a second solution, an electrophilic crosslinker, in embodiments a multi-arm PEG functionalized with electrophilic groups such as n-hydroxysuccinimide, may be prepared in a buffer such as Hanks Balanced Salt Solution, Dulbecco's Modified Eagle's Medium, Phosphate Buffered Saline, water, phosphate buffer, combinations thereof, and the like. The electrophilic crosslinker, in embodiments a multi-arm PEG functionalized with n-hydroxysuccinimide groups, may be present in a solution including the above buffer at a concentration from about 0.02 grams/mL to about 0.5 grams/mL, in embodiments from about 0.05 grams/mL to about 0.3 grams/mL.

The two components may be combined, wherein the electrophilic groups on the multi-arm PEG crosslink the amine nucleophilic components of the collagen and/or gelatin. The ratio of natural component to electrophilic component may be from about 0.01:1 to about 100:1, in embodiments from about 1:1 to about 10:1.

The nucleophilic component, which may be the natural components, e.g., collagen, gelatin, and/or hyaluronic acid, may together be present at a concentration of at least about 1.5 percent by weight of the hydrogel, in embodiments from about 1.5 percent by weight to about 20 percent by weight of the hydrogel, in other embodiments from about 2 percent by weight to about 10 percent by weight of the hydrogel. In certain embodiments, collagen may be present from about 0.5 percent to about 7 percent by weight of the hydrogel, in further embodiments, from about 1 percent to about 4 percent by weight of the hydrogel. In another embodiment, gelatin may be present from about 1 percent to about 20 percent by weight of the hydrogel, in further embodiments, from about 2 percent to about 10 percent by weight of the hydrogel. In yet another embodiment, hyaluronic acid and collagen combined as the natural component(s) may be present from about 0.5 percent to about 8 percent by weight of the hydrogel, in further embodiments, from about 1 percent to about 5 percent by weight of the hydrogel. It is also envisioned that the hyaluronic acid may not be present as a "structural" component, but as more of a bioactive agent. For example, hyaluronic acid may be present in solution/gel in concentrations as low as 0.001 percent by weight of the solution/gel and have biologic activity.

The electrophilic crosslinker may be present in amounts of from about 0.5 percent by weight to about 20 percent by weight of the hydrogel, in embodiments from about 1.5 percent by weight to about 15 percent by weight of the hydrogel.

The hydrogels may be formed either through covalent, ionic or hydrophobic bonds. Physical (non-covalent) crosslinks may result from complexation, hydrogen bonding, desolvation, Van der Waals interactions, ionic bonding, combinations thereof, and the like, and may be initiated by mixing two precursors that are physically separated until combined in situ, or as a consequence of a prevalent condition or change in the physiological environment, including temperature, pressure, pH, ionic strength, combinations thereof, and the like. Thus, the hydrogel may be sensitive to these environmental conditions/changes. Chemical (covalent) crosslinking may be accomplished by any of a number of mechanisms, including: free radical polymerization, condensation polymerization, anionic or cationic polymerization, step growth polymerization, electrophile-nucleophile reactions, combinations thereof, and the like.

In some embodiments, hydrogel systems may include biocompatible multi-precursor systems that spontaneously crosslink when the precursors are mixed, but wherein the two or more precursors are individually stable for the duration of the deposition process. In other embodiments, hydrogels may be formed from a single precursor that crosslinks with endogenous materials and/or tissues.

The crosslinking density of the resulting hydrogel may be controlled by the overall molecular weight of the crosslinker and natural component and the number of functional groups available per molecule. A lower molecular weight between crosslinks, such as 600 daltons (Da), will give much higher crosslinking density as compared to a higher molecular weight, such as 10,000 Da. Elastic gels may be obtained with higher molecular weight natural components with molecular weights of more than 3000 Da. IT should be noted that 1 Dalton is equivalent to 1 g/mol and the terms may be used interchangeably when referring to molecular weight.

The crosslinking density may also be controlled by the overall percent solids of the crosslinker and natural component solutions. Increasing the percent solids increases the probability that an electrophilic group will combine with a nucleophilic group prior to inactivation by hydrolysis. Yet another method to control crosslink density is by adjusting the stoichiometry of nucleophilic groups to electrophilic groups. A one to one ratio may lead to the highest crosslink density, however, other ratios of reactive functional groups (e.g., electrophile:nucleophile) are envisioned to suit a desired formulation.

The hydrogel thus produced may be bioabsorbable. For example, hydrogels of the present disclosure may be absorbed from about one day to about 18 months or longer. Absorbable polymers materials include both natural and synthetic polymers, as well as combinations thereof.

In embodiments, one or more precursors having biodegradable linkages present in between functional groups may be included to make the hydrogel biodegradable or absorbable. In some embodiments, these linkages may be, for example, esters, which may be hydrolytically degraded. The use of such linkages is in contrast to protein linkages that may be degraded by proteolytic action. A biodegradable linkage optionally also may form part of a water soluble core of one or more of the precursors. Alternatively, or in addition, functional groups of precursors may be chosen such that the product of the reaction between them results in a biodegradable linkage. For each approach, biodegradable linkages may be chosen such that the resulting biodegradable biocompatible crosslinked polymer degrades or is absorbed in a desired period of time. Generally, biodegradable linkages may be selected that degrade the hydrogel under physiological conditions into non-toxic or low toxicity products.

Biodegradable gels utilized in the present disclosure may degrade due to hydrolysis or enzymatic degradation of the biodegradable region, whether part of the natural component or introduced into a synthetic electrophilic crosslinker. The degradation of gels containing synthetic peptide sequences will depend on the specific enzyme and its concentration. In some cases, a specific enzyme may be added during the crosslinking reaction to accelerate the degradation process. In the absence of any degradable enzymes, the crosslinked polymer may degrade solely by hydrolysis of the biodegradable segment. In embodiments in which polyglycolate is used as the biodegradable segment, the crosslinked polymer may degrade in from about 1 day to about 30 days depending on the crosslinking density of the network. Similarly, in embodiments in which a polycaprolactone-based crosslinked network is used, degradation may occur over a period of time from about 1 month to about 8 months. The degradation time generally varies according to the type of degradable segment used, in the following order: polyglycolate<polylactate<polytrimethylene carbonate<polycaprolactone. Thus, it is possible to construct a hydrogel with a desired degradation profile, from a few days to months, using different degradable segments.

Where utilized, the hydrophobicity generated by biodegradable blocks such as oligohydroxy acid blocks or the hydrophobicity of PPO blocks in PLURONIC™ or TETRONIC™ polymers utilized to form the electrophilic precursor may be helpful in dissolving small organic drug molecules. Other properties which will be affected by incorporation of biodegradable or hydrophobic blocks include: water absorption, mechanical properties and thermosensitivity.

In other embodiments, the precursors utilized to form the hydrogel may be non-degradable, e.g., they may include any of the macromers, polymers or cores described above as suitable for use in forming the electrophilic precursor, but possess no ester or other similar degradable linkage. The non-biodegradable linkages may be created through the reaction of an N-hydroxysuccinimidyl carbonate. In one embodiment, the reaction of a multi-arm polyol with a N,N'-dihydroxysuccinimidyl carbonate creates an N-hydroxysuccinimidyl carbonate. The N-hydroxysuccinimidyl carbonate can then be further reacted with a high molecular weight polyamine such as collagen, aminated hyaluronic acid, gelatin, dextran and to create the preformed hydrogel.

High molecular weight polyamines may provide longer implant stability as compared to lower molecular weight polyamines. High molecular weight polyamines include molecular weights from about 15,000 g/mol to about 250,000 g/mol, in certain embodiments, from about 75,000 g/mol to about 150,000 g/mol. It should be understood that when a non-biodegradable linkage is used, the implant is still biodegradable through use of a biodegradable first hydrogel precursor such as collagen. More specifically, the collagen may be enzymatically degraded, breaking down the hydrogel, making the hydrogel susceptible to erosion or encapsulation.

Synthetic materials that are readily sterilized and avoid the dangers of disease transmission involved in the use of natural materials may also be used. Indeed, certain polymerizable hydrogels made using synthetic precursors are within the purview of those skilled in the art, e.g., as used in commercially available products such as FOCALSEAL® (Genzyme, Inc.), COSEAL® (Angiotech Pharmaceuticals), and DURASEAL® (Confluent Surgical, Inc). Other known hydrogels include, for example, those disclosed in U.S. Pat. Nos. 6,656,200; 5,874,500; 5,543,441; 5,514,379; 5,410,016; 5,162,430; 5,324,775; 5,752,974; and 5,550,187.

As noted above, in embodiments a multi-arm PEG, sometimes referred to herein as a PEG star, may be included to form a hydrogel utilized in forming at least a portion of a wound closure device of the present disclosure. A PEG star may be functionalized so that its arms include biofunctional groups such as amino acids, peptides, antibodies, enzymes, drugs, or other moieties in its cores, its arms, or at the ends of its arms. The biofunctional groups may also be incorporated into the backbone of the PEG, or attached to a reactive group contained within the PEG backbone. The binding can be covalent or non-covalent, including electrostatic, thiol mediated, peptide mediated, or using known reactive chemistries, for example, biotin with avidin.

Amino acids incorporated into a PEG star may be natural or synthetic, and can be used singly or as part of a peptide. Sequences may be utilized for cellular adhesion, cell differentiation, combinations thereof, and the like, and may be useful for binding other biological molecules such as growth factors, drugs, cytokines, DNA, antibodies, enzymes, combinations thereof, and the like. Such amino acids may be released upon enzymatic degradation of the PEG star.

These PEG stars may also include functional groups as described above to permit their incorporation into a hydrogel. The PEG star may be utilized as the electrophilic crosslinker or, in embodiments, be utilized as a separate component in addition to the electrophilic crosslinker described above. In embodiments, the PEG stars may include electrophilic groups that bind to nucleophilic groups. As noted above, the nucleophilic groups may be part of a natural component utilized to form a hydrogel of the present disclosure.

In some embodiments, a biofunctional group may be included in a PEG star by way of a degradable linkage, including an ester linkages formed by the reaction of PEG carboxylic acids or activated PEG carboxylic acids with alcohol groups on a biofunctional group. In this case, the ester groups may hydrolyze under physiological conditions to release the biofunctional group.

The wound plug, and/or a coating on a portion thereof, may thus be a hydrogel formed from one precursor (as by free radical polymerization), two precursors, or made with three or more precursors, with one or more of the precursors participating in crosslinking to form the elongate body and/or plug member, or participating to form a coating or layer over the elongate body and/or plug member.

The wound plugs may comprise foams, scaffolds, or other porous substrates which may be utilized instead of or in addition to a hydrogel. Foams may have an open cell structure where the pores are connected to each other, forming an interconnected network. Conversely, foams of the present disclosure may be closed-cell foams where the pores are not interconnected. Closed-cell foams are generally denser and have a higher compressive strength. Suitable techniques for forming wound plugs are within the purview of those skilled in the art and include lyophilization, particulate leaching, compression molding, phase separation, gas foaming (e.g., internal blowing agents such as $CO_2$), or through the use of a porogen (e.g., salt particles). In certain embodiments, foams which are used as tissue scaffolds can also be created through computer aided design techniques including solid freeform fabrication (SFF).

The wound plug degradation profile can be tailored to allow cells to proliferate while the implant degrades over time. One skilled in the art can alter the degradation profile of the wound plug by changing various parameters including but not limited to polymer composition and chemistry, density, morphology, molecular weight, size, porosity and pore size, wettability and processing parameters. It is also envisioned that the different portions of the plug may degrade at different rates, for example, a distal most portion of the plug may degrade faster than a proximal most portion of the plug.

Wound plugs of the present disclosure may further include a mesh for supporting injured tissue, promoting cell infiltration and tissue in growth, and in certain embodiments, preventing adhesions. More specifically, at least a distal portion of the plug may comprise a mesh, for adhesion prevention and optionally, tissue ingrowth. The mesh may comprise fibrous materials such as filaments or threads. Filaments of the mesh may be monofilament or multifilament. Where multifilament constructs are utilized, they may be braided, weaved, twisted, laid parallel, or otherwise entangled to create a fabric, mesh, textile, or patch.

The mesh may comprise natural or synthetic, bioabsorbable or non-bioabsorbable materials including those listed herein. Suitable meshes include a collagen composite mesh such as PARIETEX™ (Tyco Healthcare Group LP, d/b/a Covidien) may be used. PARIETEX™ Composite mesh is a 3-dimensional polyester weave with a resorbable collagen film bonded on one side. Other suitable meshes include those sold under the names PARIETENE®, PERMACOL™, PARIETEX™, SURGIPRO™, PRO-GRIP™ Self-fixating mesh, (all commercially available from Covidien); PROLENE™ (commercially available from Ethicon, Inc.); MARLEX®, DULEX®, 3D MAX® mesh, PERFIX® plug, VENTRALEX®, and KUGEL® patch (all commercially available from C.R. Bard, Inc.); COMPOSIX®, SEPRAMESH®, and VISILEX® (commercially available from Davol, Inc.); (DUALMESH®, MYCROMESH®, and INFINIT® mesh (all commercially available from W.L. Gore).

Methods for making woven and non-woven mesh are with the purview of those skilled in the art include weaving, knitting, spinning, felting, extruding and the like.

The mesh may be incorporated therein at least one of the portions using methods such as film casting, dip coating and over-molding. As will be described later, according to one embodiment of the present disclosure, a mesh may be incorporated into at least a distal portion of the wound plug to support the abdomen wall. The mesh may act as a tissue scaffold, providing tissue ingrowth and tissue integration. Thus, where a hydrogel of the present disclosure is utilized as a tissue scaffold, it may assist in native tissue regrowth by providing the surrounding tissue with needed nutrients and bioactive agents. In some embodiments, as discussed herein, the hydrogel itself may include a natural component such as collagen, gelatin, hyaluronic acid, combinations thereof, and the like, and thus the natural component may be released or otherwise degrade at the site of implantation as the tissue scaffold degrades.

Turning now to the Figures, a wound plug according to one embodiment of the present disclosure is illustrated in FIG. 1A. The wound plug 10 comprises a generally elongate body, which includes a distal portion 12, an intermediate portion 14, and a proximal portion 16 and may include sections within each of the portions 14, 14, and 16. Although shown as generally elongate, the wound plug 10 may also have other shapes such as, for example, cylindrical, oval, spherical, rectangular, trapezoidal, and polygonal. The wound plug 10 is generally cylindrical in cross-sectional area, although other cross-sectional areas such as rectangular, hemispherical, circular, and polygonal are envisioned.

The distal 12, intermediate 14 and proximal portions 16 are interconnected by a perforated region 21. A series of perforations 20 extend across the diameter "d1" of the wound plug 10, creating a perforated region 21. The perforations 20 illustrated are generally oblong in shape, although other geometries are envisioned including linear or ovular slits/spacings. The perforations 20 comprise hollow spaces or slits which are configured to enable breakage or tearing along the same plane as the perforations 20. When the wound plug comprises other geometries, the perforated region 21 may extend across the thickness or width of the plug. The perforated region 21 extends across a transverse (or horizontal) axis of the plug and in embodiments, extends across the diameter "d1" of the wound plug 10, enabling the plug 10 to tear along the perforated region 21, separating into multiple portions. As illustrated, the perforations 20 run generally align with and may be parallel to a tissue plane, so that when inserted, the tissue planes may move, exerting force on the wound plug 10, spatially separating portions 12, 14, and 16 such that portions 12, 14, and/or 16 may be axially and/or radially separated. It is also envisioned that when wound plug 10 is inserted in tissue planes, the movement of the tissue planes may cause a number of portions 12, 14 or 16 to spatially separate while a number of portions 12, 14 or 16 remain coupled. It is further envisioned that the movement of tissue planes may cause the sections within portions 12, 14, or 16 to separate axially and/or radially. Although a series of perforations 20 are illustrated, it is also envisioned that at least one (larger) perforation may be utilized. FIG. 1A illustrates three portions (distal 12, proximal 16, and intermediate 14), however, it is also envisioned that the plug 10 may comprise at least two portions, e.g., a distal and a proximal portion. Alternatively, more than three portions may be connected therebetween by perforated regions such that the wound plug may have several intermediate portions.

Figure 1B:
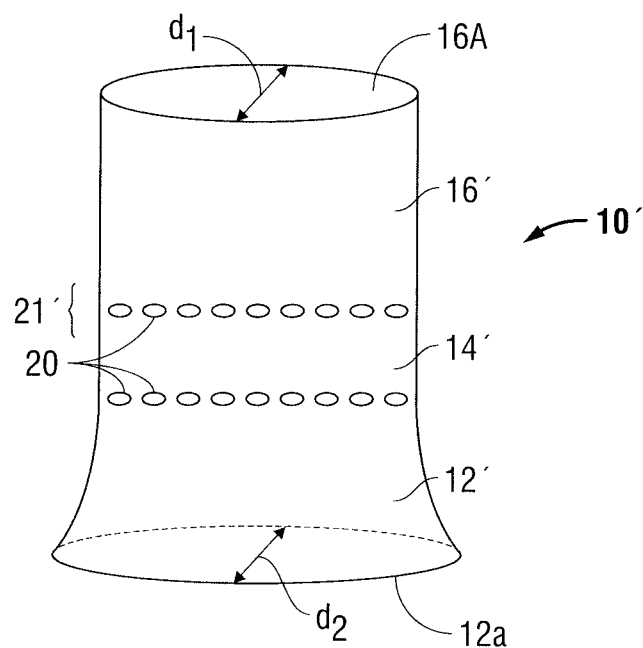
FIG. 1B illustrates an alternate embodiment of a wound plug in accordance with the present disclosure.

FIG. 1B is an alternate embodiment of wound plug 10 (FIG. 1A) and is referenced as wound plug 10'. The wound plug 10' includes a distal portion 12', an intermediate portion 14', and a proximal portion 16' and may include sections within each of the portions 12', 14', and 16'. The distal portion 12' illustrated in FIG. 1B has a larger diameter "d2" compared to the diameter "d1" at the proximal portion 16'. Similarly, the cross-sectional area of at least a distal-most surface 12a of the distal portion 12' is larger than the cross-sectional area of at least a proximal-most surface 16a of the proximal portion 16'. Similarly, the diameter of the wound plug 10' may taper from the distal portion 12' to the proximal portion 16'. In certain embodiments, it also envisioned that the wound plug may taper from the proximal portion to the distal portion. It may be preferable for the distal portion 12' and/or the proximal portion 16' to have a larger cross-sectional area for better securement of the wound plug 10' in situ.

As previously mentioned, the portions may comprise similar or different materials, which may have different mechanical properties. For example, the distal portion may have increased or decreased mechanical properties (i.e., modulus, stiffness, elasticity) as compared to the proximal portion. In other embodiments, the distal portion may further include a mesh or an anti-adhesion coating. Alternatively, the portions may comprise different materials, compositions or constructs (i.e., varying porosity).

Further, wound plugs of the present disclosure are sized and dimensioned to be received within a trocar insertion site. The plugs may be a variety of lengths and diameters, sized to accommodate patients have varying tissue thicknesses. In embodiments, the wound plugs may have a length from about 10 mm to about 150 mm and the plug member may have a diameter from about 5 mm to about 36 mm, in embodiments the elongate body may have a length from about 30 mm to about 80 mm and the plug member may have a diameter from about 10 mm to about 15 mm, and in other embodiments the elongate body may have a length from at least 10 mm and the plug member may have a width from about at least 5 mm. In one particular embodiment, the elongate body may have a width of about 39 mm and a length of about 50 mm. The plugs may be generally ovular in cross-sectional area, although other shapes are envisioned.

Certain embodiments of the wound plug may comprise an alignment member. The alignment member assists in maintaining alignment of the portions by mechanically coupling the portions together during at least insertion of the wound closure device. The alignment member may be in the form of a removable sleeve or sheath which surrounds the portions and keeps the portions generally aligned for insertion. In other embodiments, the alignment member may comprise a monomer or polymer such as an adhesive/sealant, which may be hydrophilic and upon contact with an aqueous environment such as tissue or saline, the monomer or polymer may solublize, enabling the portions to spatially separate. The portions may be reversible connected together, meaning they may be mechanically coupled together in a first position, and in the second position, the portions are spatially separated. Suitable materials include those discussed above.

In yet alternate embodiments, the alignment member may comprise an elongate body such as a fiber or suture, which may be disposed along a centerline of the portions.

Figure 2A:
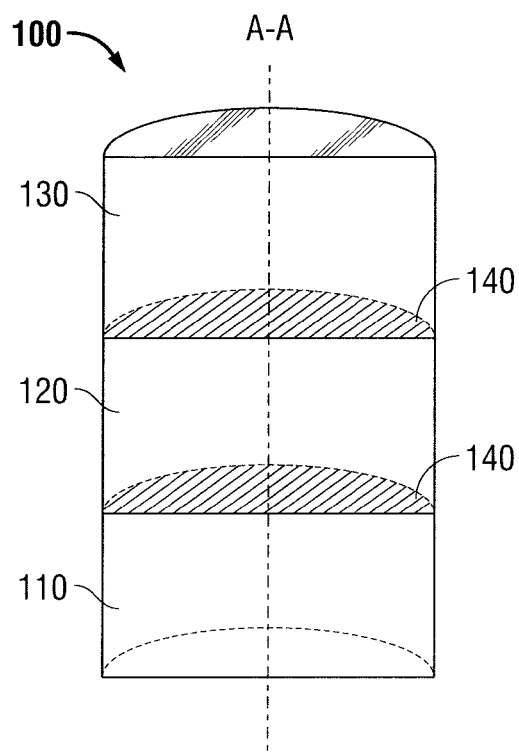
FIGS. 2A-2D illustrate cross-sectional views of different embodiments of wound plugs in accordance with the present disclosure.
Figure 2B:
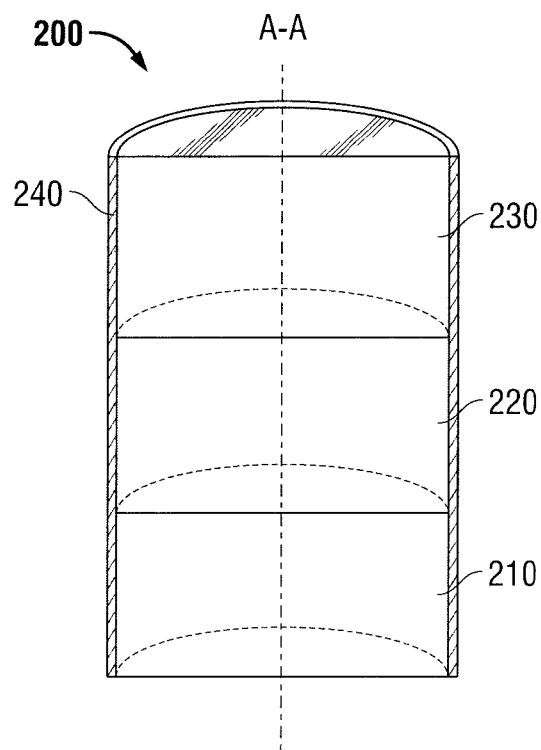
Figure 2C:
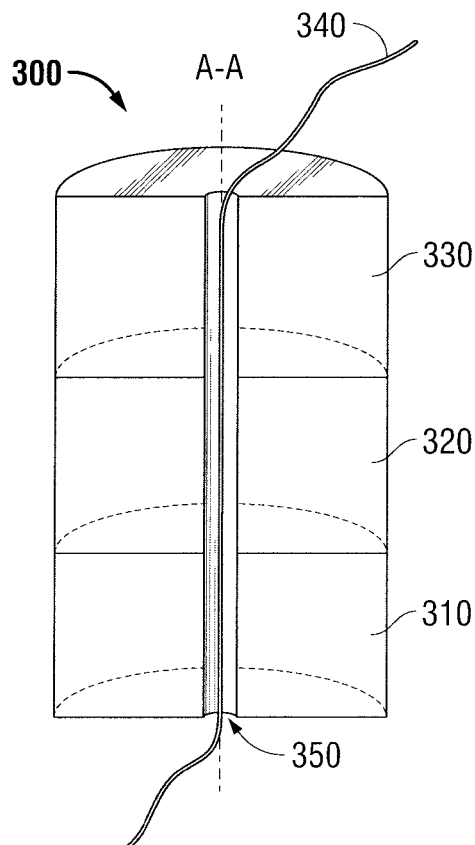

FIGS. 2A-C illustrate cross-sectional views of wound plugs comprising different alignment members. Wound plugs illustrated include portions which are separate structures, not interconnected through perforations. The alignment member mechanically couples the portions, retaining the portions in alignment along a vertical axis 'A-A' for insertion and positioning. In certain embodiments, upon spatial separation, the alignment members may either be removable or dissolvable.

More specifically, FIG. 2A illustrates a cross-sectional view of a wound plug 100 including a distal portion 110, an intermediate portion 120, and a proximal portion 130. Additionally, each portion 110, 120, and 130 may include sections. An alignment member 140 is disposed between distal portion 110 and intermediate portion 120, and between intermediate portion 120 and proximal portion 130. The alignment member 140 is illustrated as a liquid or gel, such as a glue or adhesive, which reversibly connects or adheres together the portions 110,120, and 130. Further, the alignment member may comprise a water soluble polymer or monomer. The alignment member 140 may retain the portions 110, 120 and 130 in a linear arrangement along the vertical axis 'A-A', mechanically coupling the portions at least for insertion. Again, wound plug 100 is generally cylindrical in shape and spherical in cross-sectional area, although other shapes and geometries are within the scope of this disclosure.

FIG. 2B illustrates a cross-sectional view of another embodiment of a wound plug 200, which also includes three portions, 210, 220 and 230 and may also include sections within each of the portions 210, 220, and 230. The alignment member 240 is a sleeve or a sheath, which mechanically couples the portions 210, 220 and 230. Similar to FIG. 1A, the portions are stacked in vertical alignment, along the axis 'A-A'. The sheath 240 surrounds or encases the distal 210, intermediate 220 and proximal 230 portions. The sheath 240 maintains alignment of the portions 210, 220 and 230 at least for insertion and placement in tissue. Once the plug is positioned in situ, the sheath 240 may be removed and the portions may spatially separate. In alternate embodiments, the sheath 240 may comprise a highly water soluble polymer, such as gelatin, which upon water contact or saturation, rapidly dissolves, enabling the portions to spatially separate upon movement of various tissue planes.

Figure 5A:
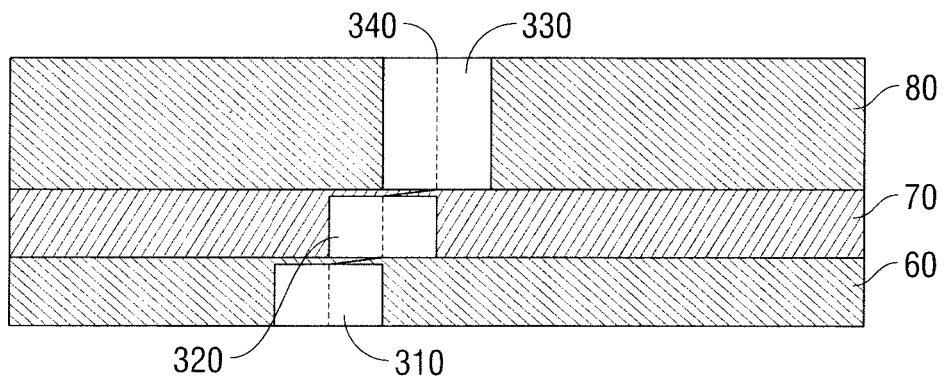
FIG. 5A illustrates a side view of FIG. 2C in tissue with the tissue planes shifted.

An alternate embodiment of a wound plug 300 is illustrated in FIG. 2C. Similar to FIGS. 2A and 2B, FIG. 2C a cross-sectional view of a wound plug 300 comprising distal, intermediate, and proximal portions 310, 320, and 330, respectively, and may also include sections within each of the portions 210, 220, and 230. The alignment member 340 is illustrated as an elongate body, such as a fiber, which assists in maintaining alignment of the portions 310, 320, and 330, along the vertical axis 'A-A'. Although shown positioned along and through a centerline of the portions, the alignment member 340 may be positioned off-center. As illustrated, the wound plug 300 includes an interior channel 350 for retaining the alignment member 340. In some embodiments, the channel 350 may be dimensioned to enable the alignment member 340 to move freely therein. Additionally, multiple alignment members 340 may be employed with multiple interior channels 350. In some embodiments, the alignment member 340 is removable, while in other embodiments, alignment member 340 is not removable, yet the alignment member 340 is positionable such that it enables the portions to spatially and/or vertically separate once inserted (FIG. 5A).

Further, the alignment member 340 may include barbs or projections (not shown), which extend outward from the elongate body. The barbs may assist in maintaining alignment of the portions in addition to maintaining the position of the alignment member 340 at least for insertion of the wound plug 300.

Figure 2D:
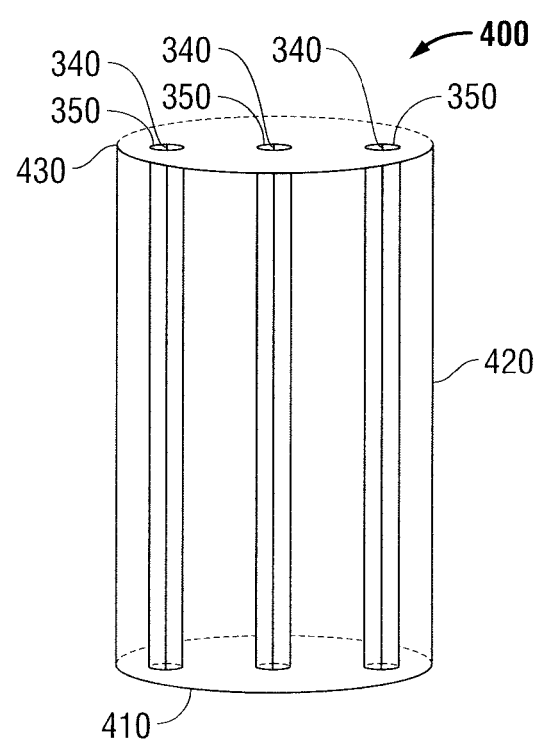
Figure 5B:
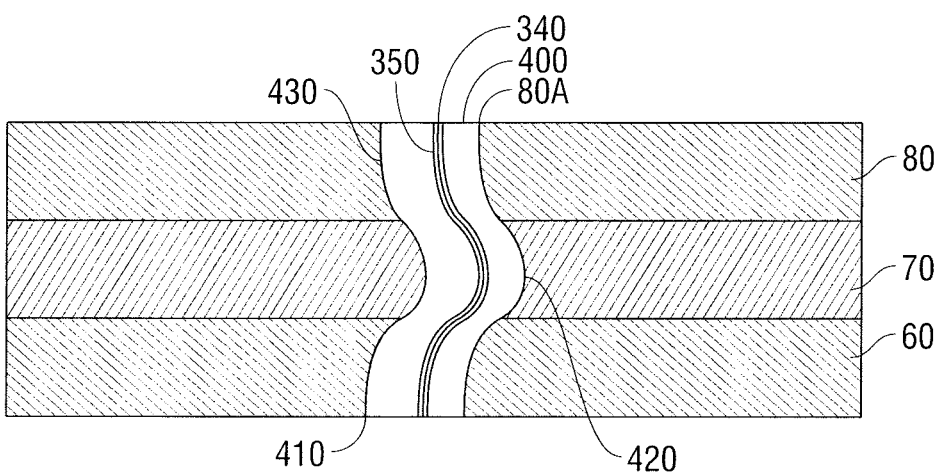
FIG. 5B illustrates a side view of the embodiment of FIG. 2D in tissue with the tissue planes shifted.

FIG. 2D illustrates a cross-sectional view of another embodiment of a wound plug 400, which also includes portions 410, 420, and 430 and may also include sections within each of the portions 410, 420, and 430. Similar to the embodiment illustrated in 2C, the alignment member 340 is illustrated as an elongate body, such as a fiber, which assists in maintaining alignment of the portions 410, 420, and 430. Although shown with three alignment members 340 retained by three interior channels 350, the wound plug 400 may include more than three alignment members 340 retained by more than three interior channels 350 or less than three alignment members 340 retained by less than three interior channels 350. In some embodiments, the alignment member 340 is removable, while in other embodiments, alignment member 340 is not removable, yet the alignment member is flexible such that it enables the portions 410, 420, and 430 to shift laterally with respect to the longitudinal axis of alignment member 340 while inhibiting wound plug 400 from shearing (FIG. 5B). It is understood that the portions 410, 420, and 430 of wound plug 400 may include different materials with different absorption rates and/or different flexibility features.

The portions may comprise similar materials (in composition), conversely, the portions may comprise different materials which have engineered biological properties the support the different tissue planes. In other embodiments, the portions may comprise varying compositions or materials to support the different tissue planes.

In embodiments, additional methods of securing a wound closure device of the present disclosure to tissue may be utilized. For example, bandages, films, gauzes, tapes, felts, combinations thereof, and the like, may be applied over a wound closure device of the present disclosure, as well as tissue surrounding the device. Similarly, additional adhesives may be applied thereto, sutures may be utilized to affix the wound plug to tissue, combinations thereof, and the like.

It is also envisioned that the embodiments illustrated in FIGS. 2A, 2B, 2C, and 2D may also have a tapered shape similar to the tapered shape described above in relation to FIG. 1B.

Bioactive agents may be added to the wound closure device to provide specific biological or therapeutic properties thereto. The term "bioactive agent," as used herein, is used in its broadest sense and includes any substance or mixture of substances that have clinical use. Consequently, bioactive agents may or may not have pharmacological activity per se, e.g., a dye, or fragrance. Alternatively, a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes.

The bioactive agents may be incorporated into the wound closure device during formation of the device, such as by free suspension, liposomal delivery, microspheres, microparticles etc., or by coating a surface of the wound closure device, or portion thereof, such as by polymer coating, dry coating, freeze drying, applying to a mesh surface, ionically, covalently, or affinity binding to functionalize the degradable components of the wound closure device. In some embodiments, bioactive agents may be incorporated within the pores of the foam or film construct. Moreover, the wound closure device may also be used for delivery of one or more bioactive agents. Thus, in some embodiments, at least one bioactive agent may be combined with a component of the wound closure device e.g., the elongate body and/or alignment member during formation to provide release of the bioactive agent during degradation of the wound closure device. As the wound closure device degrades or hydrolyzes in situ, the bioactive agents are released.

Tissue damage or tissue voids may have the potential to form adhesions during certain healing periods. Foam structures of the present disclosure may be chemically tailored to have anti-adhesive properties, which may assist in preventing adjacent tissue walls from adhering together, preventing adhesions at a wound site. In various embodiments, the foam structures may be combined with anti-adhesive materials or other bioactive agents.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the implantable medical device and the surrounding tissues opposite the target tissue. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Other bioactive agents which may be included in accordance with the present disclosure include: antimicrobials, local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; antispasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anticonvulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (p-IFN, (a-IFN and Y-'FN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

In embodiments, the polymers forming the wound closure device, such as precursors and/or hydrogels formed from the precursors, may contain visualization agents to improve their visibility during surgical procedures. Visualization agents may be selected from a variety of nontoxic colored substances, such as dyes, suitable for use in implantable medical devices. Suitable dyes are within the purview of those skilled in the art and may include, for example, a dye for visualizing a thickness of the hydrogel as it is formed in situ, e.g., as described in U.S. Pat. No. 7,009,034. In some embodiments, a suitable dye may include, for example, FD&C Blue #1, FD&C Blue #2, FD&C Blue #3, FD&C Blue #6, D&C Green

6, methylene blue, indocyanine green, other colored dyes, and combinations thereof. It is envisioned that additional visualization agents may be used such as fluorescent compounds (e.g., fluorescein or eosin), x-ray contrast agents (e.g., iodinated compounds), ultrasonic contrast agents, and MRI contrast agents (e.g., Gadolinium containing compounds).

The visualization agent may be present in any precursor component solution. The colored substance may or may not become incorporated into the resulting hydrogel. In embodiments, however, the visualization agent does not have a functional group capable of reacting with the precursor(s).

In embodiments, the bioactive agent may be encapsulated by polymers utilized to form the wound closure device. For example, the polymer may form microspheres around the bioactive agent.

Suitable bioactive agents may be combined with the wound plug either prior to or during the manufacturing process. Bioactive agents may be admixed or combined with polymers to yield a plug with bioactive properties. In other embodiments, the bioactive agent may be combined with the present disclosure for example, in the form of a coating, after the plug has been shaped. It is envisioned that the bioactive agent may be applied to the present disclosure in any suitable form of matter, e.g., films, powders, liquids, gels and the like.

Wound plugs according to the present disclosure may be manufactured using several methods. For example, the plugs may be created through use of techniques including but not limited to injection molding, compression molding, extrusion, blow molding, film blowing, thermoforming, calendaring, spinning, solvent welding, and film casting.

In embodiments where the wound plug comprises a preformed hydrogel, the wound plug may be created by simultaneously spraying the first precursor and the second precursor into a mold of a desired geometry. The first precursor and second precursor cross-linked to form a hydrogel network within 0.5 seconds to about 2 minutes, and in embodiments, from about 5 seconds to about 20 seconds.

Wound plugs according to the present disclosure may also comprise other additives such as buffers and solvents which may assist in creating the device.

Once the implant is constructed, it can be sterilized by any means within the purview of those skilled in the art including but not limited to ethylene oxide, electron beam (e-beam), gamma irradiation, autoclaving, plasma sterilization and the like.

Wound plugs of the present disclosure may be compressible and are capable of undergoing a change in shape. The plug may be configured to change shape from a first compressed shape when inserted in tissue for delivery to a second, expanded shape for maintaining its secured placement. For example, in certain embodiments, the wound plugs may comprise hydrogels or expandable foams. Upon penetration of a tissue wall, the wound plug may expand to seal a tissue defect. Wound plugs of the present disclosure also are shaped so as to limit movement proximally through a tissue wall, once inserted. The wound plug may be constructed of a material which expands from heat or fluid (polymer hydrogels) contact; alternately, the wound plug may be mechanically compressed through use of a member such as a sleeve e.g. introducer, wherein upon removal of the sleeve, the plug expands.

Figure 3:
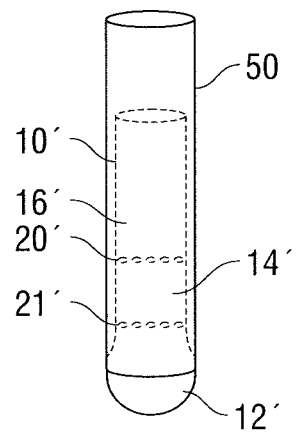
FIG. 3 illustrates a side view of FIG. 1B in a first, compressed shape for insertion, surrounded by a sheath.

Wound closure devices of the present disclosure may be inserted with the assistance of an introducer (insertion device). FIG. 3 illustrates wound plug 10' as compressed in a sleeve 50. It is understood that other embodiments of the presently disclosed wound closure device may also be compressed by a sleeve for insertion into tissue. The sleeve 50 may be employed to retain the wound plug 10' in a first, compressed shape for insertion/delivery. The sleeve 50 also extends over the portions 12', 14', and 16'. As illustrated, the distal portion 12' slightly protrudes distally from the sheath 50, however, in other embodiments, the sheath may entirely cover or retain the distal portion 12'. It is understood that the sleeve or sheath 50 may include bioabsorbable material similar to the presently disclosed bioabsorbable materials.

Figure 4A:
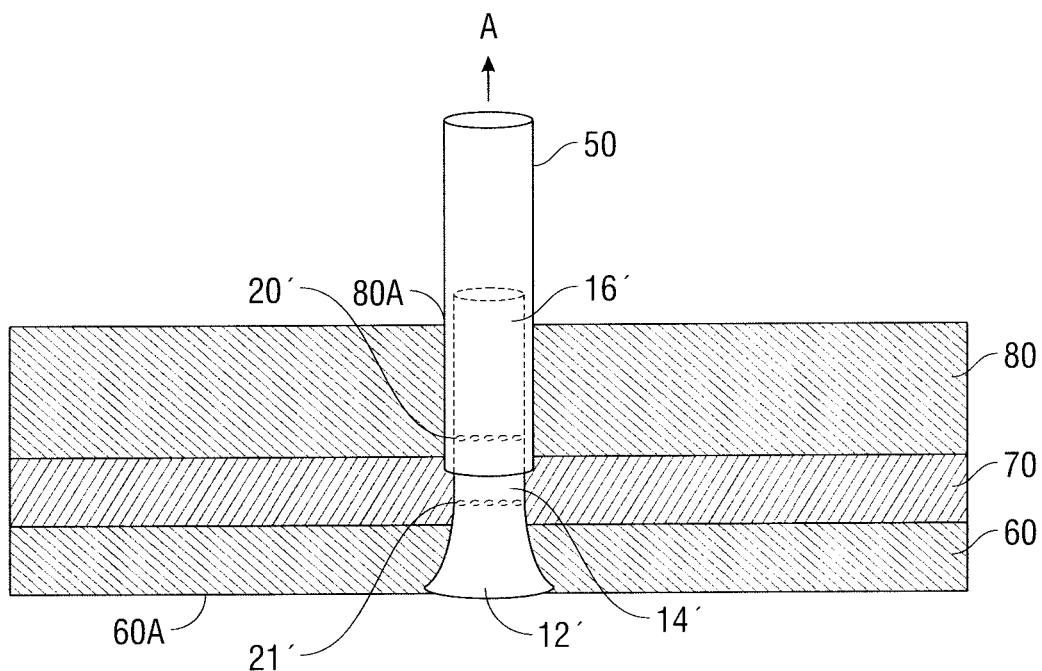
FIG. 4A illustrates a side view of the embodiment of FIG. 3 being inserted through multiple tissue planes.

FIG. 4A illustrates the sheath 50 with the compressed wound plug 10' as inserted through an opening in the tissue 80A. Upon traversing tissue layers 80, 70, and 60 and penetrating a tissue wall 60A, the sleeve 50 may be removed (retracted in the direction of the arrow A). It is understood that other embodiments of the presently disclosed wound closure device may also be inserted into the tissue in a similar manner as described herein. As previously discussed, the wound plug 10' includes a series of perforations 20', extending across the width of the elongate body 10'. The series of perforations 20' define a perforated region 21' which extends generally parallel to a tissue plane (FIG. 4A). More, specifically, the perforated region 21' is generally disposed between tissue planes 60 and 70, and again between 70 and 80.

Figure 4B:
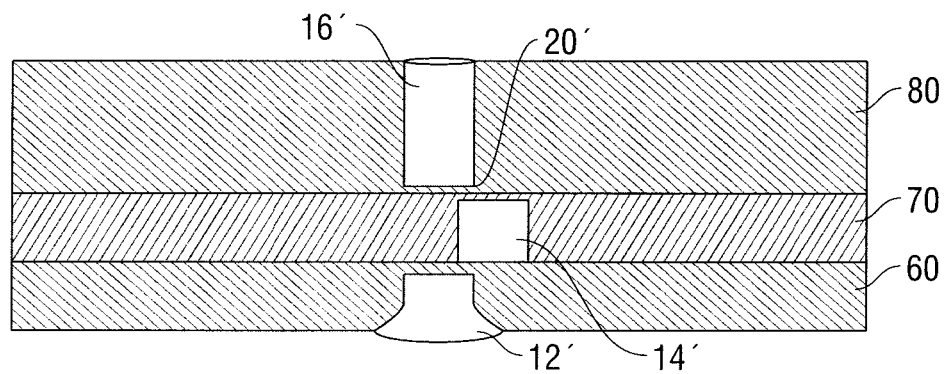
FIG. 4B illustrates a side view of the embodiment of FIG. 1B as inserted through multiple tissue planes with the tissue planes shifted.

As illustrated in FIG. 4B, upon movement of the various tissue planes 60, 70, and 80, the portions 12', 14', and 16' may tear or otherwise separate along the series of perforations 20', axially and/or radially separating the portions 12', 14', and 16'. It is further envisioned that movement of the various tissue planes 60, 70, and 80 may cause movement of the sections within the portions 12', 14, and 16' thus axially and/or radially separating all or some of the sections within portions 12', 14', and 16'. It is also envisioned that the movement of some tissue planes may cause tearing or separation along one series of perforations 20' while the movement of other tissue planes may not cause tearing or separation along another series of perforations 20' resulting in portions of the wound plug 10' being separated and portions of the wound plug 10' remaining coupled.

FIG. 5A illustrates the embodiment of FIG. 2C, in a second, spatially separated position. The wound plug 300 may be inserted into tissue using an inserter similar to that above-described. The alignment member 340 may assist in retaining the portions 310, 320, and 330 in vertical alignment during insertion. Once inserted, the portions may vertically and/or horizontally spatially separate, moving with the different tissue planes. More specifically, the distal portion may support a first tissue plane 60, the intermediate portion 320 may support a second tissue plane 70, and the proximal portion 330, may support a third tissue plane 80. The alignment member 340 may be removable, or as illustrated, the alignment member may be disposed between the tissue planes, while staying connected to the portions 310, 320, and 330. Optionally, the alignment member 340 can be tied off (not shown) at either one or both of the tissue planes 60 or 80.

FIG. 5B illustrates the embodiment of FIG. 2D, in a second laterally flexed position, after being inserted through an opening in the tissue 80A. Although not illustrated, the wound plug 400 may be inserted into the tissue using a sleeve 50 as previously described. The one or more alignment members 340 may assist in retaining the portions 410, 420, and 430 in vertical alignment during insertion. Additionally, the one or more alignment members 340 may provide additional structural support to the wound plug 400 to assist in inhibiting shearing of the wound plug 400 during insertion and after movement of the tissue planes 60, 70, and 80. Upon movement of the tissue planes 60, 70, and 80, the wound plug 400 flexes laterally. More specifically, the shifting of the one or more tissue planes 60, 70, and 80 relative to each other will cause one or more portions 410, 420, and/or 430 of wound plug 400 to shift laterally relative to each other. It is further envisioned that the shifting of the one or more tissue planes 60, 70, and 80 relative to each other may cause one or more sections within the portions 410, 420, and 430 of the wound plug 400 to shift laterally relative to each other. The lateral flexing or shifting between the portions 410, 420, and 430 and/or the sections within the portions 410, 420, and 430 of wound plug 400 may not cause a separation between the portions 410, 420, and 430 due to the structural support offered by the alignment member 340. Additionally, the portions 410, 420, and 430 may include different materials to alter the flexibility properties with respect to the force exerted by the tissue planes 60, 70, and 80 to cause shifting between the portions 410, 420, and 430.

It should be understood that various combinations of elongate bodies and plug members may be used to fabricate the wound closure device according to the present disclosure. For example, any of the elongate bodies of the embodiments described above may be combined with any of the plug members also described above, dependent upon the type of wound to be treated and the properties desired from the wound closure device.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments of the present disclosure. Various modifications and variations of the wound closure device, as well as methods of forming the elongate body and plug member of the wound closure device and attaching the components together, will be apparent to those skilled in the art from the foregoing detailed description. Such modifications and variations are intended to come within the scope and spirit of the claims appended hereto.

What is claimed is:

1. A wound plug, comprising:
   an elongate body having a plurality of portions; and
   an alignment member coupling the plurality of portions together, the alignment member including a rapidly dissolving sleeve configured to engage and maintain at least two portions of the plurality of portions in a stacked alignment, wherein the rapidly dissolving sleeve dissolves upon contact with water.

2. The wound plug of claim 1, wherein the elongate body has a first position where the plurality of portions are aligned with each other, and a second position wherein at least a section of one portion is laterally out of alignment with an adjacent portion.

3. The wound plug of claim 1, wherein the elongate body has a first position wherein the plurality of portions are operably coupled to each other, and a second position wherein at least a section of one portion is axially or radially spaced apart from an adjacent portion.

4. The wound plug of claim 1, further comprising a mesh attached to the wound plug.

5. The wound plug of claim 1, further comprising a bioactive agent attached to the wound plug.

6. The wound plug of claim 1, wherein the wound plug is compressible.

7. The wound plug of claim 1, wherein the rapidly dissolving sleeve retains the wound plug in a compressed shape.

8. The wound plug of claim 1, wherein the rapidly dissolving sleeve surrounds the plurality of portions.

9. The wound plug of claim 1, wherein the rapidly dissolving sleeve is absorbable.

10. The wound plug of claim 1, wherein the plurality of portions are stacked in a vertical alignment.

11. The wound plug of claim 1, wherein the plurality of portions are configured to be disposed in axially abutting relation.

12. The wound plug of claim 1, wherein the rapidly dissolving sleeve is formed of a highly water soluble polymer.

13. The wound plug of claim 12, wherein the highly water soluble polymer is gelatin.

14. A wound plug comprising:
   an elongate body having a plurality of portions; and
   an alignment member coupling the plurality of portions together, the alignment member including a rapidly dissolving sleeve configured to engage and maintain at least two portions of the plurality of portions in a stacked alignment, wherein the rapidly dissolving sleeve dissolves upon saturation.

* * * * *